United States Patent
Lorentzen Cornelius et al.

[11] Patent Number: 6,068,634
[45] Date of Patent: May 30, 2000

[54] STENT DELIVERY SYSTEM

[75] Inventors: Linda R. Lorentzen Cornelius, Wayzata; Katherine M. Bauermeister, Maple Grove, both of Minn.

[73] Assignee: SciMed Life Systems, Inc., Maple Grove, Minn.

[21] Appl. No.: 08/917,027

[22] Filed: Aug. 22, 1997

Related U.S. Application Data

[63] Continuation-in-part of application No. 08/702,149, Aug. 23, 1996.

[51] Int. Cl.[7] ............................................. A61F 11/00
[52] U.S. Cl. ...................................... 606/108; 606/198
[58] Field of Search ................................ 606/194, 195, 606/198, 108; 604/96

[56] References Cited

U.S. PATENT DOCUMENTS

| | | |
|---|---|---|
| 4,328,056 | 5/1982 | Snooks . |
| 4,338,942 | 7/1982 | Fogarty . |
| 4,423,725 | 1/1984 | Baran et al. . |
| 4,608,984 | 9/1986 | Fogarty . |
| 4,733,665 | 3/1988 | Palmaz . |
| 4,735,665 | 4/1988 | Miyauchi et al. . |
| 4,740,207 | 4/1988 | Kreamer . |
| 4,744,366 | 5/1988 | Jang . |
| 4,848,343 | 7/1989 | Wallsten et al. . |
| 4,875,480 | 10/1989 | Imbert . |
| 4,950,227 | 8/1990 | Savin et al. . |
| 5,007,926 | 4/1991 | Derbyshire . |
| 5,026,377 | 6/1991 | Burton et al. . |
| 5,037,392 | 8/1991 | Hillstead . |
| 5,049,132 | 9/1991 | Shaffer et al. . |
| 5,057,092 | 10/1991 | Webster . |
| 5,108,416 | 4/1992 | Ryan et al. . |
| 5,116,318 | 5/1992 | Hillstead . |
| 5,158,548 | 10/1992 | Lau et al. . |
| 5,195,969 | 3/1993 | Wang et al. . |
| 5,226,880 | 7/1993 | Martin . |
| 5,226,889 | 7/1993 | Sheiban . |
| 5,242,399 | 9/1993 | Lau et al. . |
| 5,290,306 | 3/1994 | Trotta et al. . |
| 5,295,962 | 3/1994 | Crocker et al. . |
| 5,306,250 | 4/1994 | March et al. . |
| 5,342,305 | 8/1994 | Shonk . |
| 5,344,402 | 9/1994 | Crocker . |
| 5,344,426 | 9/1994 | Lau et al. . |
| 5,358,487 | 10/1994 | Miller . |
| 5,378,237 | 1/1995 | Boussignac et al. . |
| 5,403,341 | 4/1995 | Solar . |

(List continued on next page.)

FOREIGN PATENT DOCUMENTS

| | | |
|---|---|---|
| 0 274 846 B1 | 7/1988 | European Pat. Off. . |
| 0 442 657 A2 | 8/1991 | European Pat. Off. . |
| 0 553 960 A1 | 8/1993 | European Pat. Off. . |
| O 707 837 A1 | 4/1996 | European Pat. Off. . |
| WO 90/05554 | 3/1990 | WIPO . |
| WO96/03072 A1 | 2/1996 | WIPO . |
| WO96/03092 A1 | 2/1996 | WIPO . |

OTHER PUBLICATIONS

Julio C. Palmaz et al., 156 *Radiology* 73 (1985), Expandable Intraluminal Graft: A Preliminary Study.

*Primary Examiner*—Michael A. Brown
*Assistant Examiner*—Justine R. Yu
*Attorney, Agent, or Firm*—Vidas, Arrett & Steinkraus, P.A.

[57] ABSTRACT

A stent delivery system to facilitate introduction and placement of a stent, including a catheter having an expandable distal portion constructed and arranged for expanding the outer diameter of the catheter from a contracted state to an expanded state: a stent positioned around the distal portion of the catheter having a contracted condition and being expandable to an expanded condition, and being sized in the contracted condition to closely surround the catheter in the contracted state, the expandable distal portion of the catheter including a balloon within which there is included on the catheter shaft at least one body of a diameter larger than the catheter shaft to which the stent and balloon are fitted, as by crimping, for holding the stent in place until it is released therefrom by expansion of the balloon.

38 Claims, 7 Drawing Sheets

U.S. PATENT DOCUMENTS

| | | |
|---|---|---|
| 5,405,380 | 4/1995 | Gianotti et al. . |
| 5,409,495 | 4/1995 | Osborn . |
| 5,415,664 | 5/1995 | Pinchuk . |
| 5,445,646 | 8/1995 | Euteneuer et al. . |
| 5,447,497 | 9/1995 | Sogard et al. . |
| 5,453,090 | 9/1995 | Martinez et al. . |
| 5,458,615 | 10/1995 | Klemm et al. . |
| 5,470,313 | 11/1995 | Crocker et al. . |
| 5,507,768 | 4/1996 | Lau et al. . |
| 5,512,051 | 4/1996 | Wang et al. . |
| 5,534,007 | 7/1996 | St. Germain et al. . |
| 5,536,252 | 7/1996 | Imran et al. . |
| 5,545,209 | 8/1996 | Roberts et al. ............ 606/108 |
| 5,591,222 | 1/1997 | Susawa et al. . |
| 5,603,721 | 2/1997 | Lau et al. ................. 606/108 |
| 5,628,755 | 5/1997 | Heller et al. ............. 606/108 |
| 5,643,278 | 7/1997 | Wijay . |

STENT DELIVERY SYSTEM

This is a Continuation-In-Part application based on U.S. Ser. No. 08/702,149 filed Aug. 23, 1996, now pending, which is incorporated herein by reference in its entirety.

BACKGROUND OF THE INVENTION

In typical PTCA procedures, a guiding catheter is percutaneously introduced into the cardiovascular system of a patient through a vessel and advanced through therein until the distal end thereof is at a desired location in the vasculature. A guidewire and a dilatation catheter having a balloon on the distal end thereof are introduced through the guiding catheter with the guidewire sliding through the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the flexible, expandable, preformed balloon is inflated to a predetermined size with a liquid or gas at relatively high pressures, such as greater than about four atmospheres, to radially compress the arthrosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be injury to or restenosis of the artery, which either necessitates another angioplasty procedure, a surgical by-pass operation, or some method of repairing or strengthening the area. To strengthen the area and help prevent restenosis, a physician can implant an intravascular prosthesis for maintaining vascular patency, commonly called a stent, inside the artery at the lesion. The stent is expanded to a larger diameter for placement in the vasculature, often by the balloon portion of the catheter. Stents delivered to a restricted coronary artery, expanded to a larger diameter by a balloon catheter, and left in place in the artery at the site of a dilated lesion are shown in U.S. Pat. No. 4,740,207 to Kreamer and U.S. Pat. No. 5,007,926 to Derbyshire, the content of which is incorporated herein by reference. Palmaz et al., 156 Radiology 73 (1985) and U.S. Pat. No. 4,733,665 describe introduction of a stent over a balloon catheter (incorporated herein by reference). A preferred stent for use with this invention is shown in PCT Application No. 960 3092 A1, published Feb. 8, 1996, the content of which is incorporated herein by reference.

The present invention is particularly directed to improved arrangements for releasably covering the ends of the stent to prevent the stent ends from flaring and snagging to better facilitate delivery thereof.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

SUMMARY OF THE INVENTION

This invention concerns apparatus suitable for delivery of stents to body cavities. In general, stents are prosthetic devices which can be positioned within a body cavity, for example, a blood vessel of the body of a living human or in some other difficultly accessible place. The stent prosthesis is formed of a generally tubular body, the diameter of which can be decreased or increased. Stents are particularly useful for permanently widening a vessel which is either in a narrowed state, or internally supporting a damaged vessel. Such stents are typically introduced into the body cavity by use of a catheter. The catheter is usually of the balloon catheter type in which the balloon is utilized to expand the stent, which is positioned over the balloon, to place it in a selected location in the body cavity. The present invention is particularly directed to improved arrangements for releasably covering/securing/attaching the stent, particularly the ends thereof, to the catheter to prevent snagging of the stent ends and to facilitate delivery thereof. The stent is held in place on the catheter and kept from flaring upward at its end(s) by means of at least one removable end covering means, or sock/sleeve, over the stent, the stent having been fitted to the catheter over the balloon, as by crimping. Most specifically, this invention is directed to improved modifications to the subject matter of the Savin U.S. Pat. No. 4,950,227 which is incorporated herein by reference.

In particular, the invention is directed to an improved stent delivery system designed to securely hold a stent over the balloon on a catheter, via the sleeve arrangements, and to protect the stent from deformation, damage or premature release during delivery intraluminally, as well as snagging during transportation. It is also a purpose of the present invention to provide for easier and smoother removal of the sleeve retaining means. The stent is formed to its lowest geometrical diameter when loaded. In one embodiment, rings or coils are placed over the ends of the stent to retain them and hold them to the balloon beneath the sleeves (unexpanded), and preferably adhered thereto, with little or no relative movement between the ID of the stent and the OD of the balloon/catheter arrangement. The sleeves aid in retaining the stent and hold the stent to the balloon (unexpanded). The rings or coils are each preferably attached (adhered) to the elastomeric socks and the other end of the sleeves are respectively attached to the catheter. Since most stents which are deformed to a low diameter will increase in diameter somewhat after being deformed (spring back), the rings/coils prevent spring back and increase the friction fit between the stent and balloon. When the balloon under the stent is inflated, the stent pushes out of the rings/coils and the sleeves are pushed down the balloon cones to allow the stent to deploy.

An alterative embodiment provides for easier and smoother removal of the sock retaining means. In this embodiment the rings or coils are placed over the cone portion of the balloon beneath the socks and preferably adhered thereto. The sleeves aid in retaining the stent and hold the stent to the balloon (unexpanded) with little or no relative movement between the ID of the stent and the OD of the balloon/catheter arrangement. The rings or coils are each preferably attached (adhered) to the elastomeric socks or sleeves. One end of the sleeves cover the ends of the stent and the other end of the sleeves are respectively attached to the catheter. When the balloon under the stent is inflated, the rings/coils, which are positioned on the tapered cone portion of the balloon, are driven primarily axially, resulting in the sleeves being pushed/pulled down the balloon cones to allow the stent to deploy. The positioning of the rings/coils on the cones of the balloon allows for more of an axial force when the balloon inflates rather then a radial force which may be the case if the rings are positioned on the ends of the stent, which may have a flatter profile as apposed to the tapered profile of the cone portion. This allows for a steadier, smoother, more controlled removal of the sleeves. Since most stents which are deformed to a low diameter will increase in diameter somewhat after being deformed (spring back), the sleeves also somewhat prevent spring back and increase the friction fit between the stent and balloon.

In a different embodiment, a polymer tube may be formed into a spiral, as by cutting molding or extruding, except for about 1–2 mm on one end; its entire length need only be about 1–2 cm. The uncut portion of the spiral, i.e., the ring end is placed over the end of the stent to retain it as already described. The other end of the coil, a portion of which may be uncut also to form a ring is attached to the catheter.

Modifications to this embodiment include replacement of the plastic ring with a metal ring or coil and replacement of the sleeve/ring with a metal or plastic coil or coiled ribbon. Short balloon cone length and/or tension on the spiral can help the spiral move off the stent when the balloon is inflated.

DESCRIPTION OF THE PREFERRED EMBODIMENTS

Figure 1:
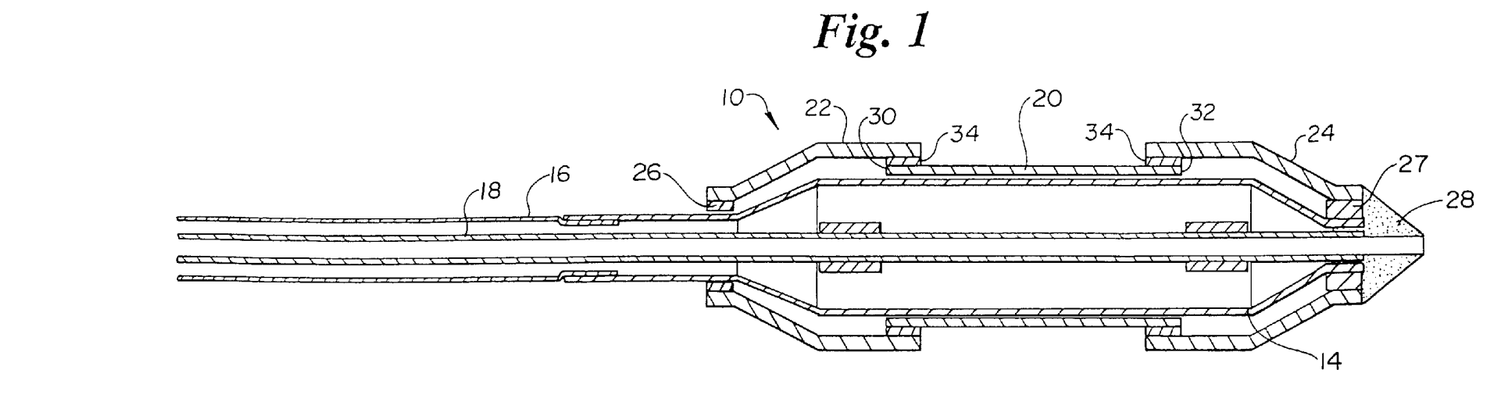
FIG. 1 is a view, in longitudinal section, of the distal end portion of a balloon catheter having a stent fixed to the catheter by being crimped thereto over the balloon, the ends of the stent being held by a first embodiment of the invention.
Figure 2:
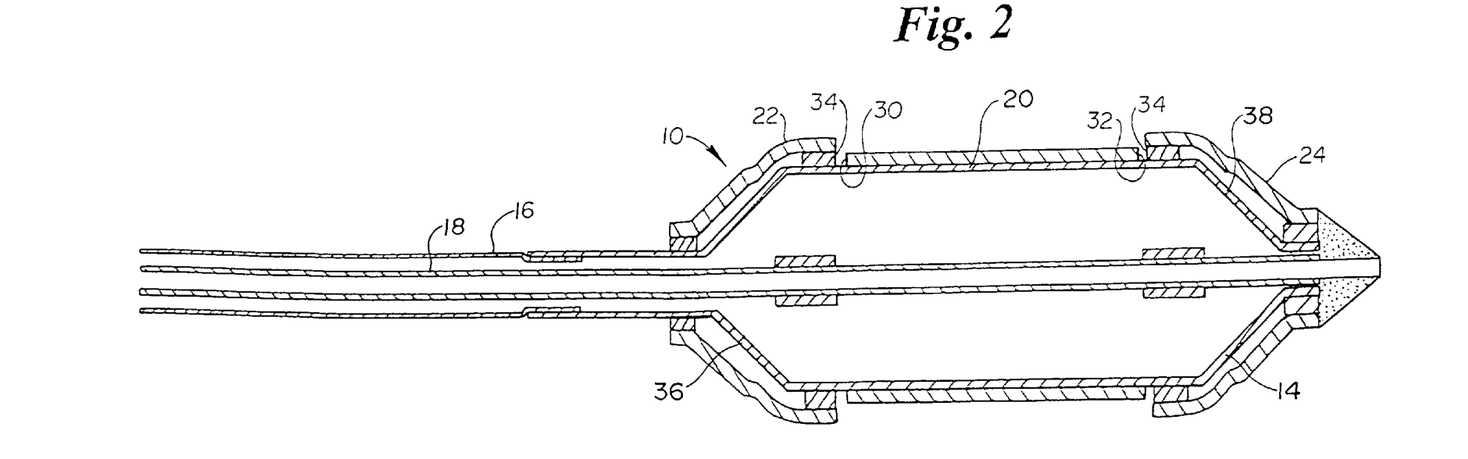
FIG. 2 is similar to FIG. 1 in which the stent has been released.

Referring to FIGS. 1 and 2, a stent delivery system 10 includes a catheter such as an over-the-wire or rapid exchange. Balloon catheters are preferred herein as best examples of catheters having an expandable distal end portion constructed and arranged for expanding the outer diameter of the catheter from a contracted state to an expanded state. A balloon 14 is fixed to the distal end of the catheter by adhesive attachment of the proximal end to the outer shaft 16 of the catheter and the distal end to the inner shaft 18 of the catheter. Other arrangements known in the art may be used. Balloon 14 is shown in FIG. 1 in its contracted state and in FIG. 2 in its expanded state. A stent 20 is fixed about balloon 14 by two overlying retaining sleeves 22 and 24.

Various types of stents may be used with balloon expansion. For example, the stent may be a self-expanding stent which upon release self-expands and is further expanded or is merely aided in release by balloon expansion from the sleeves. Such stents may self-expand elastically or may be thermally induced such as stents formed of Nitinol or other shape memory metals or materials.

Any kind of stent may be delivered by the system of the invention, including plastically deformable or elastically deformable and they may be of any configuration or structure so long as they can be loaded at a low diameter and deployed at a larger diameter, i.e., have a contracted condition and being expandable to an expanded condition of large diameter.

Stent 20 may be any of the various types known in the art, either balloon expandable or self-expandable. Exemplary stents are shown in U.S. Pat. No. 4,735,665; U.S. Pat. No. 4,950,227; EPO application No. 707 837 A1, and U.S. Pat. No. 5,445,646. All of these patents are incorporated herein by reference and are intended to be exemplary only and not limiting. Various materials including stainless steel, tantalum, shape memory alloys and plastic may be used.

Stent 20 is radially compressed, as by crimping to a contracted condition, against balloon 14 to a relatively small loaded diameter having an OD of 0.044 inches for example, although it has a larger released diameter in the expanded condition.

Sleeves 22 and 24 may be formed of polyurethane tubing or the like, having for example an ID of 0.032–0.038 inches and a wall thickness of 0.002–0.004 inches, for example, and are axially fixed along catheter 10 to the proximal end of balloon 14 at 26 and to the distal end of balloon 14 at 27 by means of polyurethane adhesive. The distal end also includes a tapered end 28 which may be formed of the same adhesive.

The sleeves may be of an expandable material, preferably elastomers such as polyurethane, silicone, latex or polyether amide, by way of example only. The material should be formable into a thin walled tube. Only one sleeve may be provided at one end of the stent, preferably the distal end. However, the use of a pair of sleeves, one at each end of the stent, is most preferred.

Sleeves 22 and 24 overlap stent 20 at each of its ends 30 and 32, respectively. For example, the overlap may be 0.5–1.5 mm. Reinforcing rings 34 are included under the overlapping portions of sleeves 22 and 24 and in contact with the stent ends. The rings may be attached to the sleeves with adhesive such as a polyurethane adhesive. The rings may be plastic, such as polyimide or polyethylene, or metal, such as platinum, gold, stainless steel or Nitinol, and may be 0.001–0.004 inches and the ID of the ring is to match the desired OD of the stent. The function of the rings is to compress the stent and hold it down.

Referring to FIG. 2, in its expanded state balloon 14 has an enlarged diameter with tapered portions 36 and 38 at each end thereof. Stent 20 is released from sleeves 22 and 24 upon expansion of balloon 14 by pulling out of the sleeves and the bunching back of the sleeves. As seen in FIG. 2 the stent deploys. The sleeves contract about balloon 14 when it is deflated. Deflation allows balloon 14 and sleeves 22 and 24 along with catheter 10 to be axially removed from the body.

In situations where the stent OD is large relative to the stretched ID of the sleeves; such as 0.060 inches as compared to 0.032–0.038, the fit between the sleeve ID and the balloon end portion tends to be so large as to create difficulty in forming an acceptable profile for the catheter and it is difficult to sufficiently increase the OD of the balloon catheter to provide adequate interference fit of the stent to the balloon. The rings provide increased friction fit in such instances and aid in controlling spring-back of the crimped stent.

In assembling the polyurethane sleeves, they can be temporarily swelled by exposure to a solvent such as toluene, alcohol, or others as known in the art, then pushed on the ends of the stent. The sleeves are then bonded to the balloon ends with a polyurethane adhesive or the like.

Figure 3:
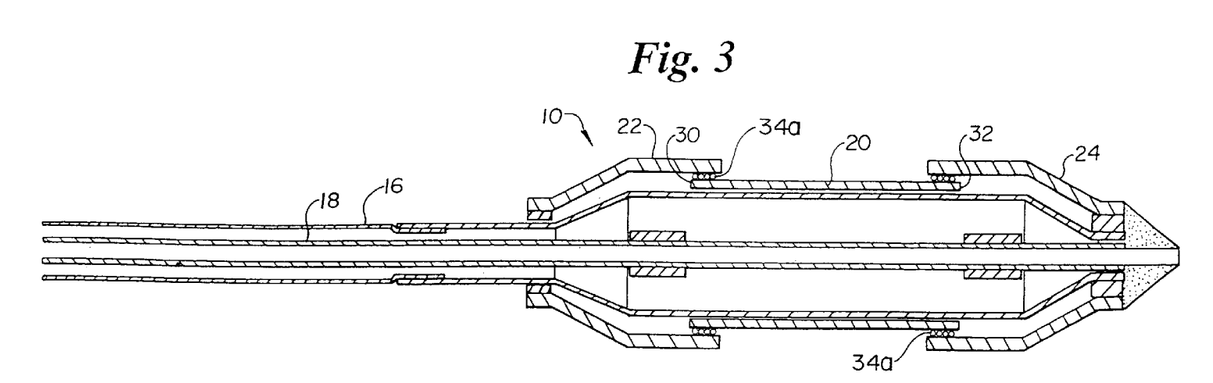
FIG. 3 is a view of a modification of the embodiment shown in FIGS. 1 and 2.

Other embodiments are within the claims to this invention. For example, referring to FIG. 3, the rings 34 seen in FIGS. 1 and 2 may take the form of wire coils 34a which may for example be stainless steel or Nitinol or polyamides such as nylon.

Figure 4:
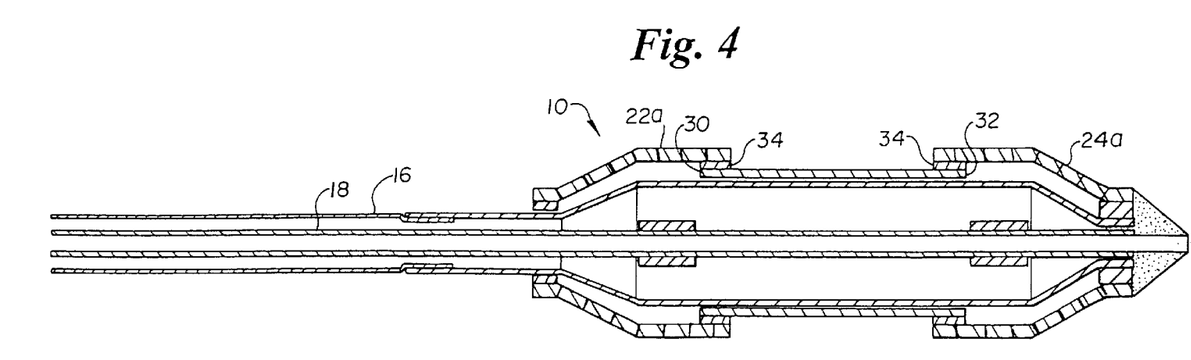
FIG. 4 is a view of another modification to the embodiment of FIGS. 1 and 2.

Referring to FIG. 4, the sleeves 22 and 24 of the preceding Figures may take the form of spiral coils of plastic 22a and 24a such as polyamide or polyethylene or polyimide for example. The spiral may be cut only partially into the body as a spiral cut or it may be cut all the way through as shown.

Figure 5:
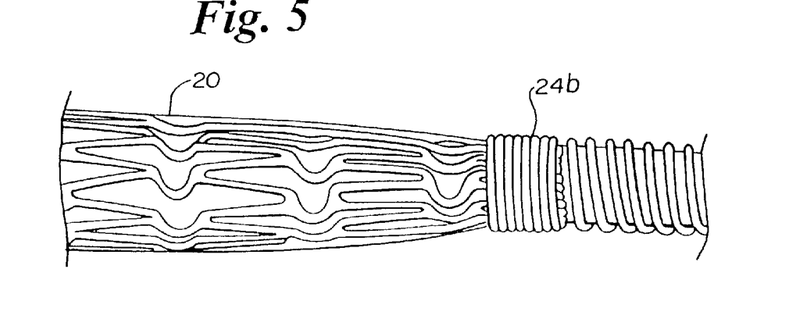
FIG. 5 is a showing of another embodiment of the invention used to hold the ends of the stent.
Figure 6:
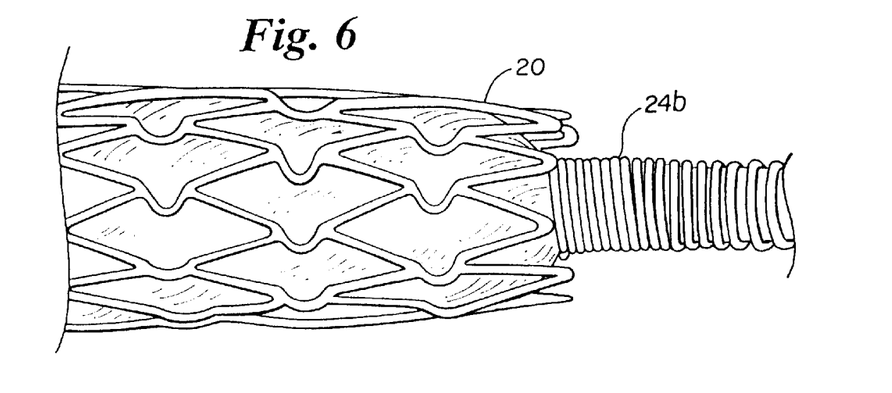
FIG. 6 is a showing of the FIG. 5 arrangement in which the stent has been released.

Referring to FIGS. 5 and 6, the sleeves 22 and 24 of the preceding Figures may be replaced by metal such as stainless steel or Nitinol coils 22b (not shown) and 24b, for example. FIG. 5 shows such coils engaging stent 20 in the loaded or crimped position, ready for delivery. FIG. 6 shows the coils retracted by balloon expansion with stent 20 partially expanded and ready to be deployed.

Figure 7:
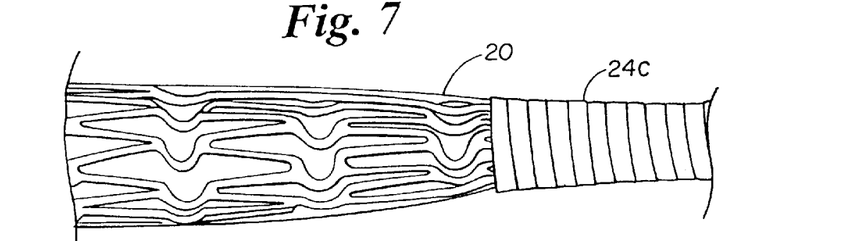
FIG. 7 is a showing of yet another embodiment of the invention used to hold the ends of the stent.
Figure 8:
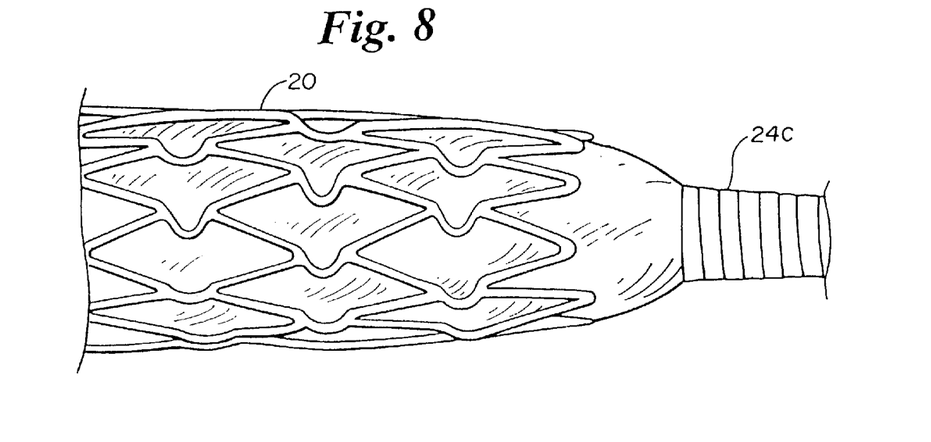
FIG. 8 is a showing of the FIG. 7 arrangement in which the stent has been released.

Referring to FIGS. 7 and 8, metal coils 22b (not shown) and 24b of FIGS. 5 and 6 may take the form of flat coiled ribbons 22c and 24c in either metal or plastic of the types already described. In FIG. 7 the coiled ribbons 22c and 24c are shown engaging the stent 20 in the loaded or crimped position, ready for delivery. FIG. 8 shows them retracted by balloon expansion with stent 20 partially expanded ready for deployment.

Figure 9:
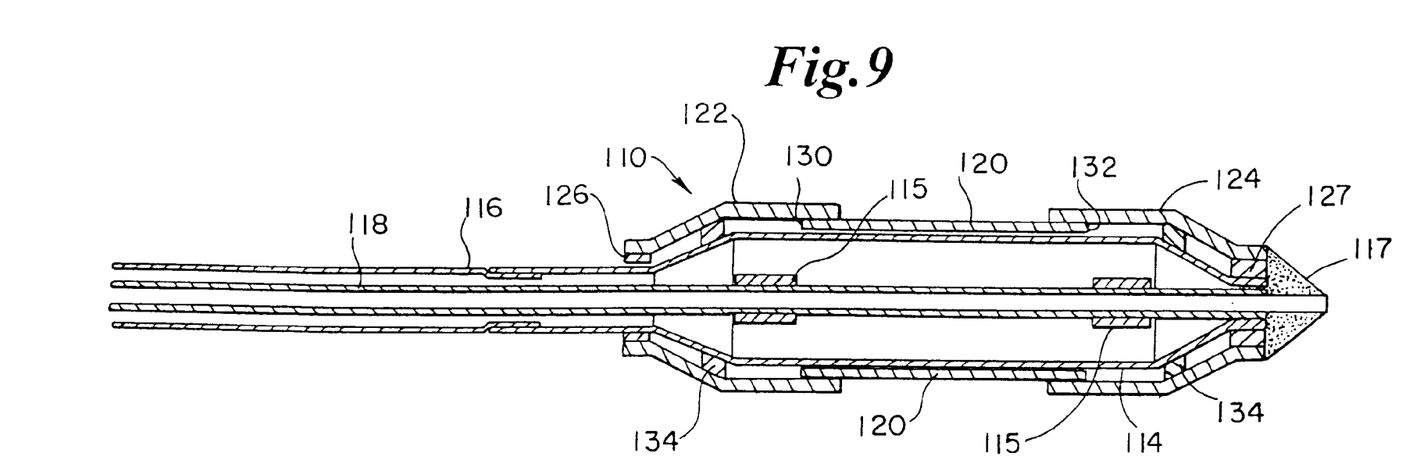
FIG. 9 is a view of an alternative embodiment, in longitudinal section, of the distal end portion of a balloon catheter having a stent fixed to the catheter by being crimped thereto over the balloon, the ends of the stent being covered by an alternate embodiment of the invention.
Figure 9A:
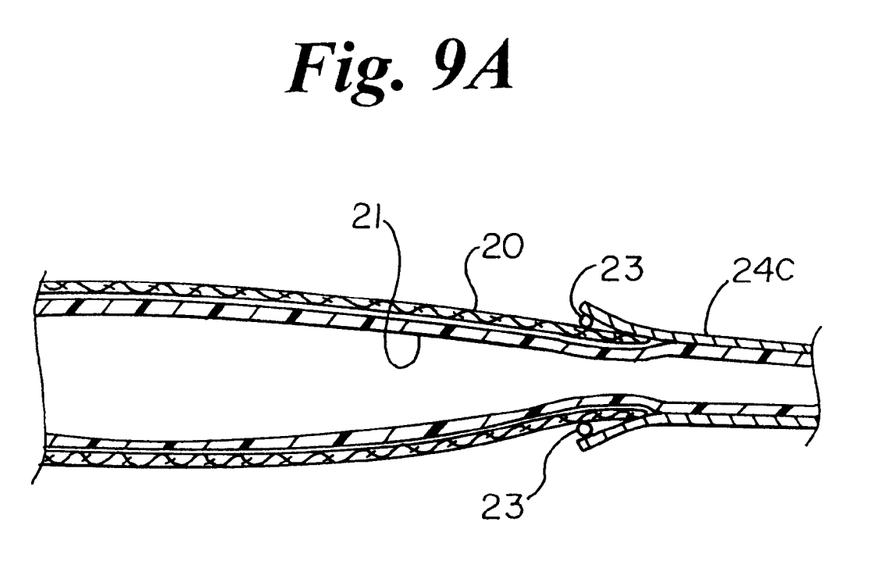
FIG. 9A is a partial cross-sectional view of FIG. 7.

FIG. 9A is a cross-sectional view of FIG. 7. It illustrates the coil 24c and a ring 23 attached to the inside of the end of the coil 24c, the combination of which secures the end of the stent 20 onto the balloon 21 prior to expansion of the balloon.

Any body compatible metal and plastic having the requisite strength characteristics, and/or other physical characteristics may be used in the various embodiments of this invention.

Figure 10:
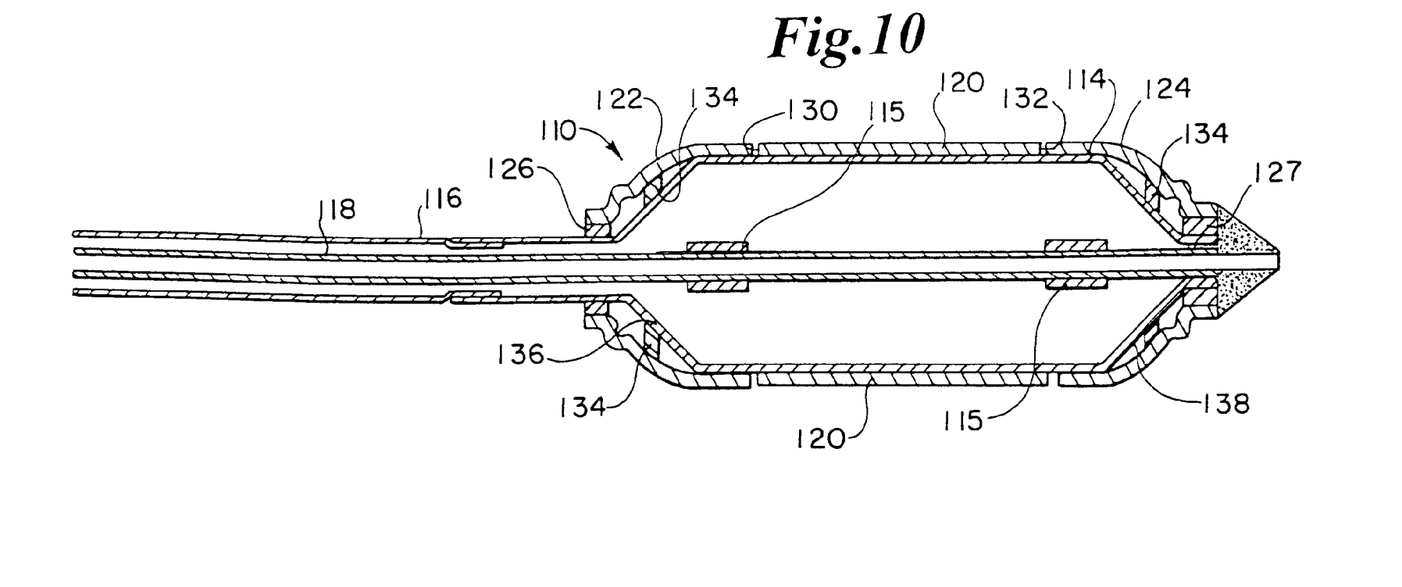
FIG. 10 is similar to FIG. 9 in which the stent has been released.
Figure 11:
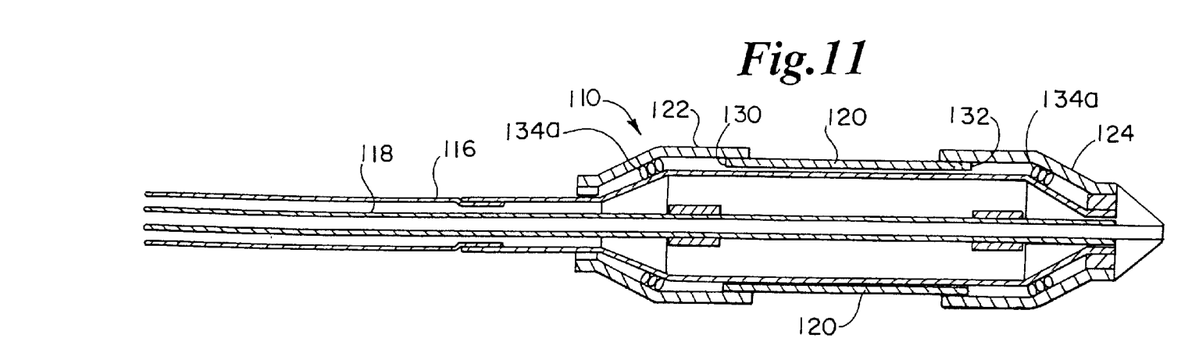
FIG. 11 is a view of a modification of the embodiment shown in FIGS. 9 and 10.

Alternative embodiments are shown in FIGS. 9–13. These embodiments are basically the same as those mentioned above, except for the positioning of the ring. Combinations of the embodiments may be employed. Referring to FIGS. 9 and 10, a stent delivery system 110 includes a catheter such as an over-the-wire or rapid exchange. Shown is a catheter 110 having a outer shaft 116, a guidewire lumen 118 with marker band secured thereto 115 and a distal tip 117. As above, balloon 114 is fixed to the distal end of the catheter by adhesive attachment of the proximal end to the outer shaft 116 of the catheter and the distal end to the inner shaft 118 of the catheter. Other arrangements known in the art may be used. Balloon 114 is shown in FIG. 9 in its contracted state and in FIG. 10 in its expanded state. A stent 120 is fixed about balloon 114 by two overlying retaining sleeves, or socks, 122 and 124, which cover the ends 130, 132 of the stent, respectively.

Various types of stents may be used with balloon expansion, as described above.

Stent 120 is radially compressed, as by crimping to a contracted condition, against balloon 114 to a relatively small loaded diameter having an OD of 0.044 inches for example, although it has a larger released diameter in the expanded condition.

As above, sleeves 122 and 124 may be formed of polyurethane tubing or the like, having for example an ID of 0.032–0.038 inches and a wall thickness of 0.002–0.004 inches, for example, and are axially fixed along catheter 110 to the proximal end of balloon 114 at 126 and to the distal end of balloon 114 at 127 by means of polyurethane adhesive 126, 127.

As above, the sleeves may be of an expandable material, preferable elastomers such as polyurethane, silicone, latex or polyether amide, by way of example only, most preferably polyurethane or polyolefin copolymer (POC); Surlyn™. The material should be formable into a thin walled tube. Only one sleeve may be provided at one end of the stent, preferably the proximal end. However, the use of a pair of sleeves, one at each end of the stent, is most preferred.

Sleeves 122 and 124 overlap stent 120 at each of its ends 130 and 132, respectively. For example, the overlap may be 0.5–1.5 mm. Rings 134 are included under, and preferably adhered to, the sleeves 122 and 124 positioned on the cone portion of the balloon 114, preferably the upper portion, when the balloon is in its collapsed configuration. The rings may be attached to the sleeves with adhesive such as a polyurethane adhesive. The rings may be rigid or any material which effectively retains its substantially annular shape, preferably non-elastomeric material, including plastic, such as polyimide or polyethylene, or metal, such as platinum, gold, stainless steel or Nitinol, and may be 0.25–0.5 mm in length and the ID of the ring is to match the desired OD of the upper portion of the cone portion. In the alternative, the sleeve material may be of a higher Durometer urethane or even merely may have a thicker annular region in the sleeve to function as a ring. The function of the rings is to more effectively and smoothly draw the sleeve off of the ends of the stent, by creating a more axial force on the ring 134.

Referring to FIG. 10, in its expanded state balloon 114 has an enlarged diameter with tapered cone portions 136 and 138 at each end thereof. Stent 120 is released from sleeves 122 and 124 upon expansion of balloon 114 due to the axial force created by the ring which draws the sleeves gradually outward, bunching the sleeve between the rings 134 and the fixed position of the sleeve on the catheter. As the balloon is inflated, a combination of radial and axial forces are applied to the ring 134. Since the rings resist the radial force, they are driven primarily axially, dragging the sleeve off of the ends of the stent and balloon. The increased axial pressure allows for a more controlled and steady release of the stent and balloon, as opposed to a sudden release which may happen when the primary force on the ring is in the radial direction. As seen in FIG. 10 the stent deploys. The sleeves contract about balloon 114 when it is deflated. Deflation allows balloon 114 and sleeves 122 and 124 along with catheter 110 to be axially removed from the body.

The positioning of the rings 134, which provides for greater axial force, allow the sleeves to be made of softer and thinner material, such as softer grades of urethanes, which include the use of lower Durometer urethane such as 65–95A or 55D (55D Durometer urethane), for example Tecothane 1055D. This is an advantage because the ring is the active movement mechanism pulling the sleeve off the balloon, releasing the stent, and by improving the flexibility of the sleeves improves the overall flexibility of the catheter, thus improving the tracking of the system through the coronary vascular. It is desirous to have the sleeve smoothly slide down the cone of the balloon without appreciably expanding.

In assembling the polyurethane sleeves, they can be temporarily swelled by exposure to a solvent such as toluene, alcohol, or others as known in the art, then pushed on the ends of the stent. The sleeves are then bonded to the balloon ends with a polyurethane adhesive or the like. The rings are either held in place by the tension between the sleeves and balloon or the rings are attached to the sleeves.

Other embodiments are within the claims to this invention. For example, referring to FIG. 11, the rings 134a seen in FIGS. 9 and 10 may take the form of wire coils 134a which may for example be stainless steel or Nitinol or polyamides such as nylon.

Figure 12:
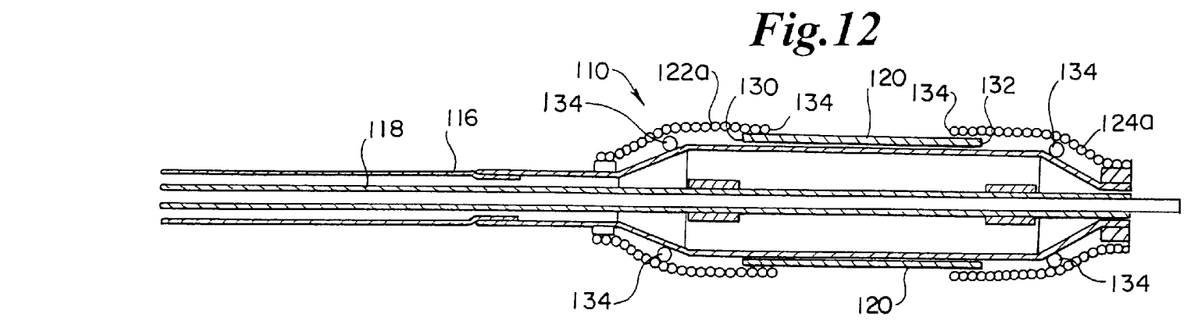
FIG. 12 is a view of another modification to the embodiment of FIGS. 9 and 10.

Referring to FIG. 12, the sleeves 122 and 124 of the preceding Figures may take the form of spiral coils of plastic 122a and 124a such as polyamide or polyethylene or polyimide for example. The spiral may be cut only partially into the body as a spiral cut or it may be cut all the way through as shown.

Figures 13A, 13B:
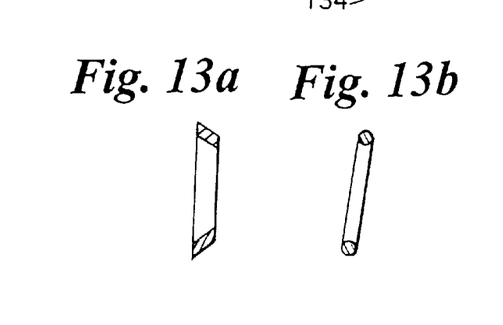
FIGS. 13a–c are side views of various ring configurations.
Figure 13C:
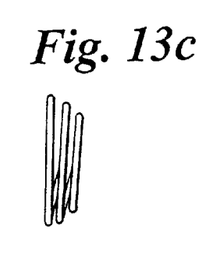

The rings 134 are preferably circular in shape, but may also be any regular polygon. FIGS. 13a–c illustrate possible designs of the rings 134. The ring of FIG. 13a has a tapered profile to conform to the cones' tapered profiles. FIG. 13b illustrates a typical tubular ring and FIG. 13c illustrates a coil ring.

Any body compatible metal and plastic having the requisite strength characteristics, and/or other physical characteristics may be used in the various embodiments of this invention.

Figure 14:
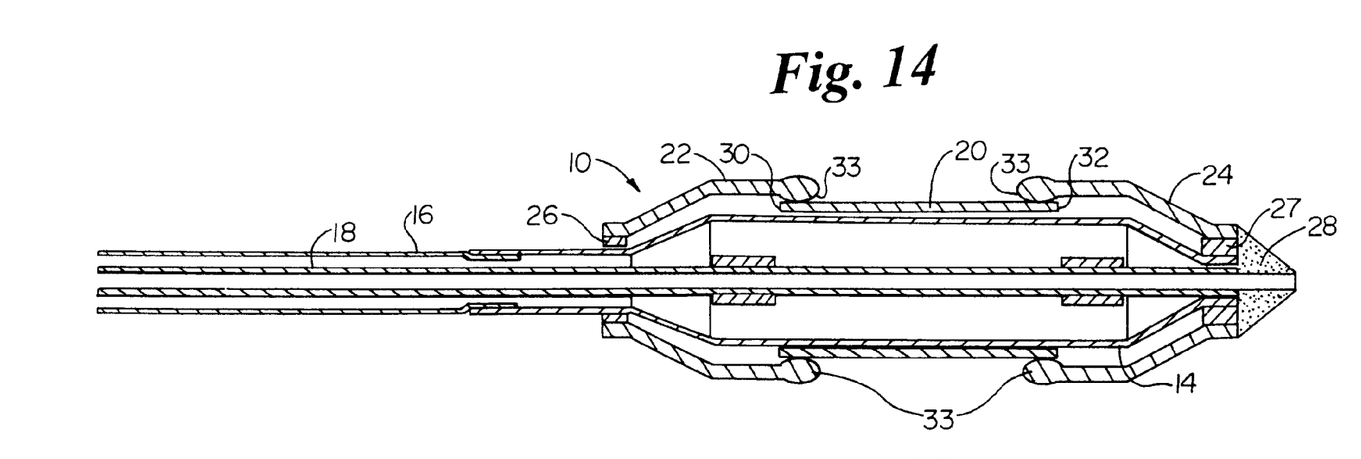
FIGS. 14 and 15 are side views of a modification of the embodiment shown in FIGS. 1 and 2.
Figure 15:
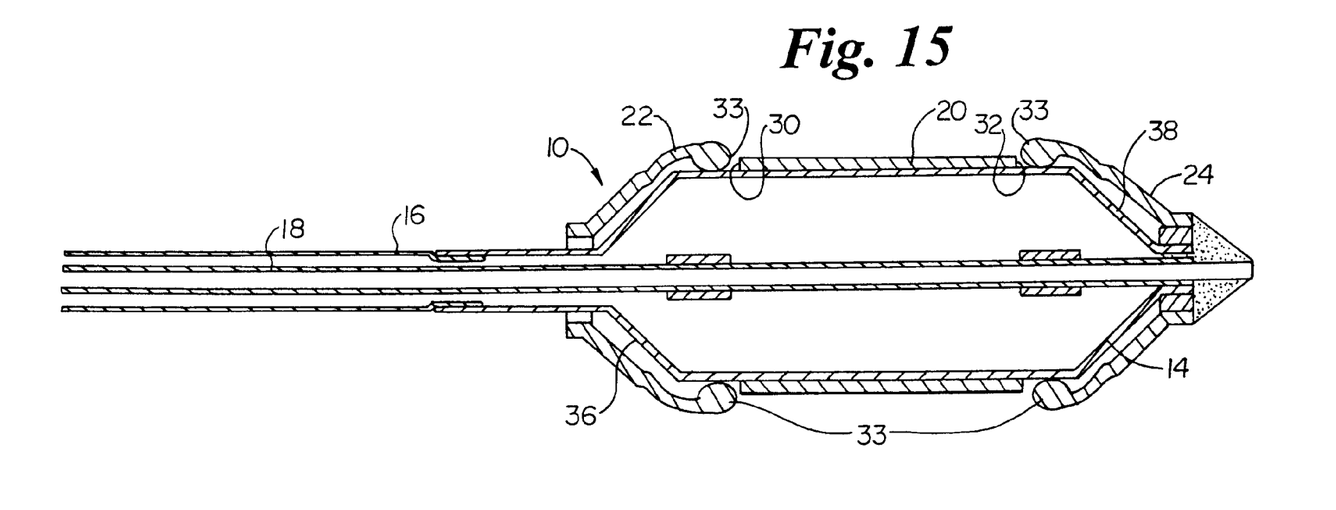

As shown in FIGS. 14 and 15, the sleeves 22, 24 may include an annular portion or region 33 of increased thickness and rigidity, wherein the annular portion 33 is integral with the sleeve material. As before, the sleeves retain the ends 30, 32 of the stent 20 on the balloon 36 when the balloon 36 is in its contracted state (see FIG. 14). When the balloon 36 expands, the sleeves 22, 24, including the thicken, rigid annular region, arc drawn off the ends 30, 32 of the stent 20, as shown in FIG. 16, thereby releasing the stent from the catheter.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the attached hereto.

What is claimed is:

1. A stent delivery system comprising:
   a catheter comprising an expandable distal portion, having an outer diameter, constructed and arranged for expanding the outer diameter of said expandable distal portion from a contracted state to an expanded state;
   a stent positioned around said distal portion of said catheter, said stent having a contracted condition and being expandable to an expanded condition, the stent being sized in said contracted condition to closely surround said expandable distal portion in its contracted state, said stent having a first end and a second end, wherein at least one of the stent ends is positioned over a portion of said expandable portion of said catheter;
   a first sleeve in the region of said distal portion of said catheter positioned around said catheter, the first sleeve having a first end anchored to said catheter, and a second end lying over said first end of said stent; and
   a first ring positioned between the first sleeve and the expandable distal portion of the catheter, said ring being attached to said first sleeve,
      said first sleeve retaining said first end of said stent on said catheter when said expandable distal portion is in the contracted state, said catheter and stent cooperatively constructed and arranged for expansion of said expandable distal portion from said contracted state to said expanded state and to cause said first sleeve and first ring to simultaneously slide relatively axially, drawing said sleeve from over said first end of said stent, thereby releasing said first end of the stent from said catheter.

2. The stent delivery system of claim 1, wherein said first ring is attached to said second end of said first sleeve and positioned around said first end of said stent and wherein said expandable distal portion comprises a balloon mounted on a shaft of the catheter, whereby said stent is expanded by expansion of said balloon.

3. The stent delivery system of claim 2, said first sleeve being formed from polyurethane.

4. The stent delivery system of claim 2, said first sleeve being formed from an elastomer material, the elastomer material being able to be expanded with a balloon angioplasty catheter, and formable into a thin-walled tube in the shape of a cylinder.

5. The stent delivery system of claim 2, the stent having a distal end and a proximal end, said first end of said stent being the distal end of the stent, wherein said first sleeve secures said distal end of the stent on the balloon when the balloon is in its contracted state.

6. The stent delivery system of claim 5 wherein the first ring is metal.

7. The stent delivery system of claim 5 wherein the first ring is plastic.

8. The stent delivery system of claim 2, said first ring being formed in the shape of a coil.

9. The stent delivery system of claim 8 wherein said coil is plastic.

10. The stent delivery system of claim 8 wherein the coil is metal.

11. The stent delivery system of claim 1, the first and second ends of the stent being positioned over said expandable portion of said catheter, the delivery system further comprising:
    a second sleeve in the region of said distal portion of said catheter and positioned around said catheter, the second sleeve having a first end anchored to said catheter, and a second end lying over said second end of said stent; and
    a second ring, the second ring being respectively attached to said second sleeve and positioned around said second end of said stent,
        said first sleeve and first ring engaging the first end of the stent and said second sleeve and second ring engaging said stent at said second end, wherein said ends of said stent are secured on said catheter when said expandable portion is in the contracted state, said catheter and stent cooperatively constructed or arranged for expansion of said expandable portion from said contracted state to said expanded state to cause expansion of said stent, including said first and second ends of said stent, from said stent's contracted condition to said expanded condition, and thereby causing said sleeves and rings to slide relatively axially from over the ends of said stent, thereby releasing said ends of the stent from said catheter.

12. The stent delivery system of claim 11 wherein said expandable distal portion comprises a balloon mounted on the catheter, whereby said stent is expanded by expansion of said balloon.

13. The stent delivery system of claim 11, said sleeves being formed from polyurethane.

14. The stent delivery system of claim 11, said sleeves being formed from an elastomer material, the elastomer material being able to be expanded with a balloon angioplasty catheter, and formable into a thin-walled tube in the shape of a cylinder.

15. The stent delivery system of claim 11, said first end of said stent being a distal end of the stent, wherein said first sleeve secures said distal end of said stent to the catheter.

16. The stent delivery system of claim 11, said first ring being formed in the shape of a coil formed of plastic or metal.

17. The stent delivery system of claim 11 wherein the first ring is metal or plastic.

18. The stent delivery system of claim 1 wherein said expandable distal portion comprises a balloon, whereby said stent is expanded by expansion of said balloon, the balloon having at least one cone portion mounted on a shaft of the catheter and wherein the first ring is positioned between the cone portion and the first sleeve when the balloon is in its contracted state.

19. The stent delivery system of claim 18, said first sleeve being formed from polyurethane.

20. The stent delivery system of claim 18, said first sleeve being formed from an elastomer material, the elastomer material being able to be expanded with a balloon angioplasty catheter, and formable into a thin-walled tube in the shape of a cylinder.

21. The stent delivery system of claim 18, said second end of said stent being a proximal end, wherein said first sleeve covers said stent at the proximal end of said stent.

22. The stent delivery system of claim 18, said first ring being formed in the shape of a coil formed of plastic or metal.

23. The stent delivery system of claim 22 wherein said first coil is plastic or metal.

24. The stent delivery system of claim 18 wherein the first ring is metal or plastic.

25. The stent delivery system of claim 1, the first and second ends being positioned over said expandable portion of said catheter, the delivery system further comprising:
   a second sleeve, said sleeves being in the region of said distal portion of said catheter and positioned around said catheter, each having a first end anchored to said catheter, and a second end lying over a said end of said stent, wherein the second end of the first sleeve lies over the first end of the stent and the second end of the second sleeve lies over the second end of the stent; and
   a second ring, the first ring and second ring each being respectively attached to said first and second sleeves and positioned between said sleeves and said expandable portion of said catheter, wherein said expandable distal portion comprises a balloon having a distal cone portion and a proximal cone portion mounted on a shaft of the catheter and wherein the first ring and the second ring are positioned between the distal cone portion and the proximal cone portion, respectively, and the respective sleeves when the balloon is in its contracted state, said first sleeve and said second sleeve separately engaging said stent at said first end and said second end, respectively, said first and second sleeves covering said first and second ends of said stent, respectively, on said expandable distal portion when said expandable distal portion is in the contracted state, and said first and second rings being attached to said first and second sleeves, respectively, between said sleeves and said expandable portion of the catheter distal and proximal to said distal and proximal ends of said stent, respectively, said catheter and stent cooperatively constructed or arranged for expansion of said expandable distal portion from said contracted state to said expanded state to cause expansion of said stent from said contracted condition to said expanded condition, and thereby causing said rings to slide relatively axially, the rings drawing said sleeves from over said ends of said stent, thereby releasing said stent from said catheter.

26. The stent delivery system of claim 25, said sleeves being formed from polyurethane.

27. The stent delivery system of claim 25, said sleeve being formed from an elastomer material, the elastomer material being able to be expanded with a balloon angioplasty catheter, and formable into a thin-walled tube in the shape of a cylinder.

28. The stent delivery system of claim 25, said rings being formed in the shape of a coil of plastic or metal.

29. The stent delivery system of claim 25 wherein the rings are metal or plastic.

30. A stent delivery system comprising:
   a catheter comprising an expandable distal portion, the expandable distal portion having an outer diameter, constructed and arranged for expanding the outer diameter of said expandable distal portion from a contracted state to an expanded state;
   a stent positioned around said distal portion of said catheter, said stent having a contracted condition and being expandable to an expanded condition, the stent being sized in said contracted condition to closely surround said expandable distal portion in the expandable distal portion's contracted state, said stent having a first end and a second end, at least one of the stent ends lying over said expandable portion of said catheter;
   a first coil in the region of said distal portion of said catheter and positioned around said catheter, having a first end anchored to said catheter, and a second end defining a margin lying over said first end of said stent; and
   a first ring attached to said second end of said coil, the ring being within the coil and overlying said stent;
   said first coil securing said first end of said stent on said expandable distal portion when said expandable distal portion is in the contracted state, said expandable distal portion and stent cooperatively constructed and arranged to cause expansion of said expandable distal portion from said contracted state to said expanded state and to cause expansion of said stent, including said first end of said stent, from said contracted condition to said expanded condition, thereby causing said first coil to slide relatively axially from over the margin of said stent, thereby releasing said first end of the stent from said catheter.

31. The stent delivery system of claim 30 wherein said first coil is plastic or metal.

32. The stent delivery system of claim 30 wherein said first coil is rounded in cross-section.

33. The stent delivery system of claim 30 wherein said first coil is ribbon-like in cross-section.

34. The stent delivery system of claim 30, wherein said expansible distal portion comprises a balloon mounted on a shaft of the catheter.

35. The stent delivery system of claim 34, wherein said stent is expanded by expansion of said balloon.

36. The stent delivery system of claims 35, the first and second ends of the stent lying over said expandable portion of said catheter, the delivery system further comprising, a second coil having a first end and a second end and a second ring attached to said second end of said second coil, wherein the second ring is within the coil, the first and second coils being in the region of said distal portion of said catheter positioned around said catheter, each having a first end anchored to said catheter and a second end defining a margin lying over said ends of said stent, said first coil and said second coil separately engaging said stent at said first end and said second end, respectively, said coils and rings securing said ends of said stent on said expandable distal portion when said expandable distal portion is in the contracted state, said expandable distal portion and stent cooperatively constructed and arranged for expansion of said expandable distal portion from said contracted state to said expanded state to cause said coils to slide relatively axially from over the margins of said stent, thereby releasing said ends of the stent from said catheter.

37. A stent delivery system comprising:
   a catheter comprising an expandable distal portion, having an outer diameter, constructed and arranged for expanding the outer diameter of said expandable distal portion from a contracted state to an expanded state;
   a stent positioned around said distal portion of said catheter, said stent having a contracted condition and being expandable to an expanded condition, and being sized in said contracted condition to closely surround said expandable distal portion in the contracted state, said stent having an end lying over an end portion of said expandable portion of said catheter; and
   a sleeve in the region of said distal portion of said catheter and positioned around said catheter, said sleeve having a first end anchored to said catheter, and a second end lying over said end of said stent, the sleeve having an annular region of increased thickness and rigidity retaining said end of said stent on said catheter when said expandable distal portion is in the contracted state, said expandable distal portion and stent cooperatively constructed and arranged for expansion of said catheter from said contracted state to said expanded state and to cause said sleeve, including the thick, rigid annular region, to slide relatively axially, drawing said sleeve from over said stent, thereby releasing said end of the stent from said catheter.

38. The stent delivery system of claim 37, wherein the annular region of increased thickness and rigidity is positioned at the second end of said sleeve.

* * * * *